(12) United States Patent
Bitterlich et al.

(10) Patent No.: US 6,462,150 B1
(45) Date of Patent: Oct. 8, 2002

(54) METHOD FOR ISOLATING OLEFINS FROM POLYOLEFIN PLANTS

(75) Inventors: Stefan Bitterlich, Dirmstein (DE); Kaspar Evertz, Schifferstadt (DE); Manfred Hecker, Neustadt (DE); Hans-Jacob Feindt, Flemington, NJ (US)

(73) Assignee: Basell Polyolefine GmbH, Kehl (DE)

( * ) Notice: Subject to any disclaimer, the term of this patent is extended or adjusted under 35 U.S.C. 154(b) by 0 days.

(21) Appl. No.: 09/913,074

(22) PCT Filed: Mar. 23, 2000

(86) PCT No.: PCT/EP00/02554

§ 371 (c)(1), (2), (4) Date: Aug. 9, 2001

(87) PCT Pub. No.: WO00/59957

PCT Pub. Date: Oct. 12, 2000

(30) Foreign Application Priority Data

Apr. 1, 1999 (DE) .......................................... 199 15 106

(51) Int. Cl.[7] .................................................. C08F 2/34
(52) U.S. Cl. ........................... 526/68; 526/348; 526/71; 526/82; 422/139; 422/171; 422/190
(58) Field of Search ........................... 526/348, 71, 68, 526/82, 901; 422/139, 171, 190

(56) References Cited

U.S. PATENT DOCUMENTS

| | | | |
|---|---|---|---|
| 4,588,790 A | 5/1986 | Jenkins, III et al. | 526/70 |
| 5,521,264 A | 5/1996 | Mehra et al. | 526/68 |
| 5,681,908 A | * 10/1997 | Mehra et al. | 526/68 |

FOREIGN PATENT DOCUMENTS

| | | |
|---|---|---|
| DE | 1 520 498 | 2/1973 |
| EP | 0 646 603 | 4/1995 |
| JP | 8-151413 | 6/1996 |
| WO | WO 99/45035 | 9/1999 |
| WO | WO 9945035 | * 9/1999 |

OTHER PUBLICATIONS

M. Jacobs et al., "Olefins Recovery in Polyolefin Plants Using Membrane Technology", (Membrane Technology & Research, Inc. Mar. 10, 1998).

* cited by examiner

*Primary Examiner*—David W. Wu
*Assistant Examiner*—William K Cheung
(74) *Attorney, Agent, or Firm*—James C. Lydon

(57) ABSTRACT

The present invention relates to a method for the isolation of olefins from a gas mixture comprising one or more olefins, inert gas and catalyst poison, where the gas mixture is fed to a separation unit (18) and separated into olefin and inert gas. The method according to the invention has the special feature that an apparatus (17) is installed upstream or downstream of the separation unit (18) and that i) in the case of an upstream apparatus (17), the catalyst poison is at least partially removed from the gas mixture, and ii) in the case of a downstream apparatus (17), the catalyst poison is at least partially removed from the separated-off olefin.

The olefins here are preferably isolated from a gas mixture formed as offgas in catalytic gas-phase polymerization for the preparation of polyolefins. The recovery of the olefins from the offgas is of economic importance.

11 Claims, 1 Drawing Sheet

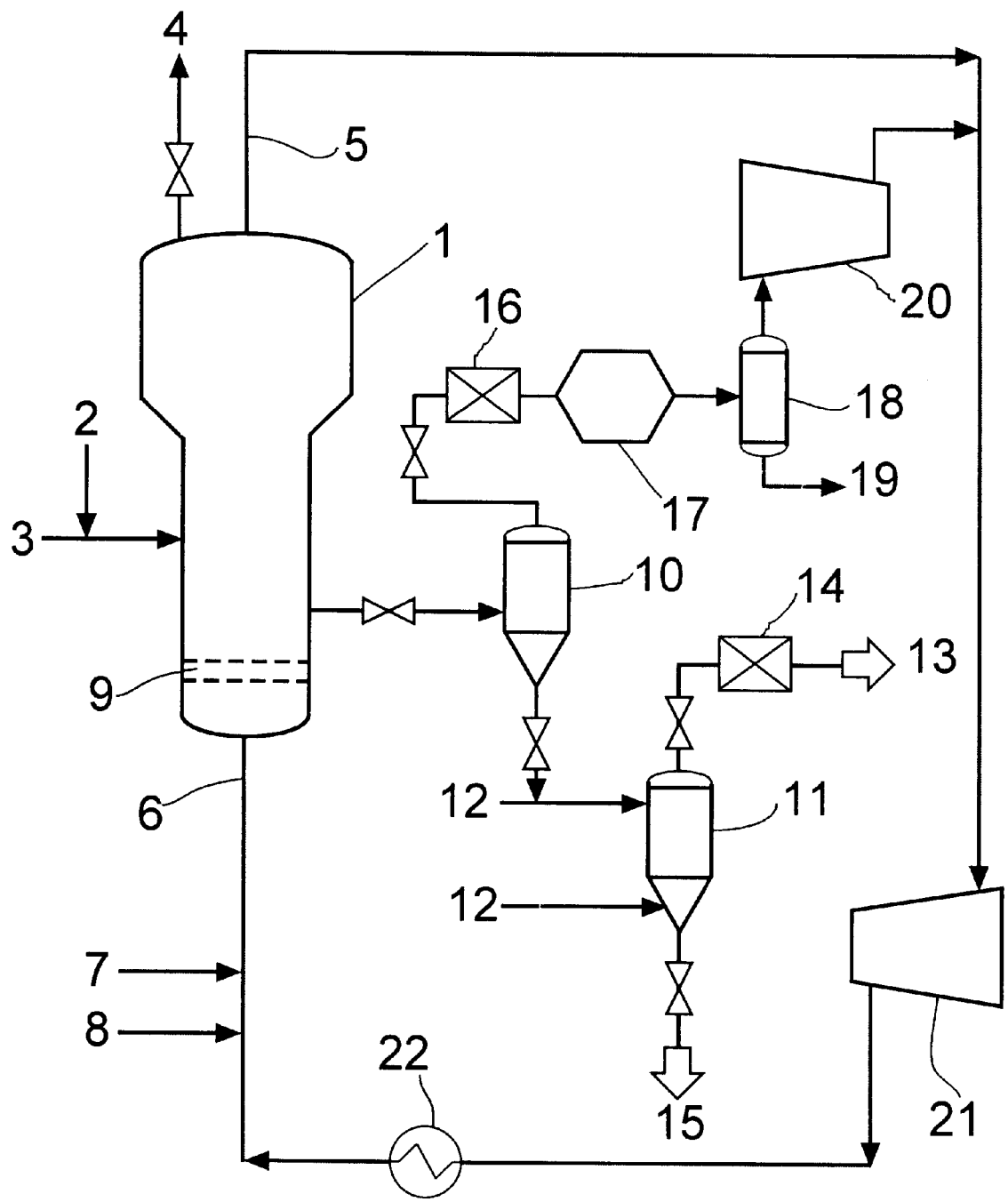

METHOD FOR ISOLATING OLEFINS FROM POLYOLEFIN PLANTS

This application is a U.S. National Stage of International Application PCT/EP00/02554, filed on Mar. 23, 2000 and published on Oct. 12, 2000 in the German language.

The present invention relates to a method for the isolation of olefins from polyolefin plants, and to a method and an apparatus for the preparation of polyolefins.

BACKGROUND OF THE INVENTION

Gas-phase polymerization is an important technology for the preparation of polyolefins. the catalyst, which is usually employed in supported form, is in the form of small, free-flowing particles which serve as starting points for the polymerization. In general, gas-phase polymerization is carried out as a fluidizedbed process. In this, the catalyst particles are in the form of a fluidized bed during the polymerization. The monomers are generally introduced with the carrier gas into the corresponding polyolefin plant, which is preferably designed as a fluidized-bed polymerization reactor. Catalyst particles are added elsewhere in the polymerization reactor, usually together with inert gas. Particularly suitable catalysts are Philipps (based on chromium/silica gel), Ziegler or metallocene catalysts. The addition of inert gas is necessary since the basic heterogeneously catalyzed polymerization is usually moisture- and/or oxygen-sensitive. The resultant polymer is produced in solid form, which means that the catalyst and polymer exist alongside one another in the fluidized bed. Unreacted monomer is usually circulated thereby dissipating the heat of the reaction.

Gas-phase polymerizations are used, for example, to prepare polyethylene or polypropylene. However, this process can also be used to prepare polymers which are composed of a plurality of different monomer units, so-called copolymers. Suitable catalysts for the gas-phase polymerization are, as described in the introduction, in particular Ziegler, Philipps and metallocene catalysts. Philipps and metallocene catalysts are very sensitive to catalyst poisons, which may suppress the polymerization even in low concentrations (in the ppm range). Catalyst poisons of this type are, for example, sulfur compounds, such as sulfur dioxide or hydrogen sulfide. These frequently occur in such small concentrations that they cannot be detected directly from the gaseous reaction mixture. It is therefore frequently difficult to judge which catalyst poisons are responsible for the inactivity of a catalyst. Since catalyst poisons generally accumulate during continuous operation of gas-phase polymerization plants, it is necessary to remove some of the gaseous reaction mixture from the reactor as offgas during operation.

The disadvantage exists here that olefins are also lost as valuable starting materials if the offgas is not worked up. The offgas in gas-phase polymerizations generally comprises predominantly inert gas and unreacted olefin. If inert gas is not partially removed from the reactor, it accumulates, since it is not reacted in the polymerization. For this reason, it is necessary to continuously remove a constant offgas stream from the reactor in continuous operation. In general, valuable olefin is removed together with inert gas and other secondary components, such as, for example, catalyst poisons, the olefin present in the gas mixture removed is subsequently burnt, and the resultant combustion gas is finally discarded. The loss of olefin is financially significant, and it has consequently been attempted to recover the olefin and to recycle it into the polymerization reactor.

The isolation of the polyolefin from the offgas can be achieved, for example, in accordance with U.S. Pat. No. 5,521,264, by extraction of the olefin, it being necessary to separate the olefin from the extractant in a next step. This separation is quite complex in equipment terms, which means that it is generally more economic and inexpensive not to separate off the olefin and to discard it (after combustion) with the offgas.

SUMMARY OF THE INVENTION

The present invention has the object of improving the generic method for the preparation of polyolefins in such a way that the polyolefins present in the offgas can be recovered and subsequently fed back into the polymerization reactor. It is of particular importance here that the recovered olefin is freed both from inert gases and from by-products, in particular catalyst poisons. The equipment complexity should be kept as low as possible here, so that the recovery of the olefins is economically viable.

This object is achieved by a method for the isolation of olefins from a gas mixture comprising one or more olefins, inert gas and catalyst poison, in which the gas mixture is fed to a separation unit and separated into olefin and inert gas. The method according to the invention is then characterized in that an apparatus is connected upstream or downstream of the separation unit and that i) in the case of an upstream apparatus, the catalyst poison is removed at least partially from the gas mixture, and ii) in the case of a downstream apparatus, the catalyst poison is removed at least partially from the separated-off olefin.

According to a preferred embodiment of the invention, the gas mixture is produced as offgas in the catalytic gas-phase polymerization of olefins.

The method according to the invention is particularly suitable if metallocene or chromium/silica gel catalysts are used for the polymerization, since these catalysts are particularly sensitive to catalyst poisons. These catalyst poisons are frequently virtually impossible to identify, which means that it is of great importance to remove even extremely small amounts of impurities, even in the ppm range, as completely as possible. In general, the proportion of the catalyst poison in the gas mixture is less than $10^{-3}\%$ by weight.

An apparatus which is particularly suitable for removing the catalyst poison in accordance with the invention is one which is designed for mass separation. The term apparatus for mass separation is intended to mean equipment which contains one or more molecular sieves which are able to adsorb, absorb or chemically bind catalyst poison. The equipment can contain, for example, molecular sieve such as activated carbon, zeolites or washing liquid. A suitable corresponding adsorption method is, in particular, pressure sowing adsorption (PSA). However, also suitable in principle are apparatuses with the aid of which catalyst poisons are chemically reacted, with the corresponding secondary products of the catalyst poisons themselves no longer being able to act as catalyst poison—apparatuses of this type can then release these secondary products again (into the gas stream). A condensation device which operates on the principle of low-temperature separation, is likewise a suitable apparatus, with, in this embodiment, the catalyst poison being removed by fractional condensation.

In the operating variant of the mass separation apparatus by the adsorption method which is particularly preferred according to the invention, the operating temperature in the loading phase is in the range from −30 to 100° C., preferably in the range from 10 to 50° C., while the pressure in this phase is in the range from 3 to 50 bar, preferably from 10 to 30 bar. In the case of operation with periodic change of the adsorbent or with periodic regeneration of the adsorbent, for example by means of nitrogen, the optimum temperatures for operation of the apparatus are, in accordance with the invention, in the range from 80 to 240° C.

Generally the offgas formed in the polymerization process essentially consists (preferably to the extent of greater than 95%) of inert gas and olefin. This gas mixture generally comprises from 20 to 80% by volume, preferably from 40 to 60% by volume, of olefin. The isolation of the olefin from the inert gas is carried out using a separation unit which is, for example, a membrane device which contains one or more membranes, or a distillation device. Membrane devices of this type for the recovery of olefins usually contain one or more diffusion membranes which retain inert gases, such as, for example, nitrogen, and are permeable to relevant olefins (generally to many organic compounds, in particular to numerous hydrocarbons) [M. Jacobs, D. Gottschlich, K. Kaschemekat, Membrane Technology & Research, Inc., Mar. 10, 1998]. The separation into olefin and inert gas is very generally incomplete, meaning both that the separated-off olefin may contain inert gas (residues), and the separated-off inert gas may contain olefin (residues). In this context, the term enrichment of the corresponding components may be used. Suitable separation units are in principle not suitable for the removal or separation of catalyst poisons—this function is taken on in accordance with the invention by a corresponding apparatus. Thus, the membrane devices employed as separation unit cannot be used for the removal or separation of catalyst poison.

Membranes which are preferred in accordance with the invention are so-called composite membranes, which essentially consist of an impermeable polymer layer, for example of a polydialkylsiloxane, such as polydimethylsiloxane or polyoctylmethylsiloxane, on a porous support material. Suitable support materials are polymers, such as polyesters, polystyrenes, polyamides or also polyolefins. The above-described membranes are employed in accordance with the invention in the form of spiral-wound flat or also cushion modules.

The membrane separation is preferably carried out at temperatures in the range from −30 to 100° C., particularly preferably from 0 to 50° C., a pressure in the range from 3 to 50 bar, preferably from 10 to 30 bar, advantageously prevailing on the feed side, while the pressure on the permeate side adopts a value of from 0.1 to 10 bar, preferably from 0.8 to 5 bar.

The olefin employed in accordance with the invention is in particular ethylene or propylene. However, it is also possible to polymerize different olefins at the same time, giving copolymers. In principle, all olefins that can be polymerized or copolymerized can be employed in accordance with the invention. Since catalytic gas-phase polymerizations are generally highly oxygen- and/or moisture-sensitive, these are usually carried out in an inert-gas atmosphere. A particularly suitable inert gas is nitrogen. In principle, however, all gases or gas mixtures which have an inerting action in the basic preparation process, for example alkanes, can be employed as inert gas. The catalyst poison separated off is preferably sulfur dioxide.

In addition, an apparatus is provided for carrying out the method according to the invention, this apparatus containing the following devices:

a) a fluidized-bed polymerization reactor,
b) a discharge tank,
c) a filter for the retention of fine polymer particles,
d) an apparatus for the removal of the catalyst poison,
e) a separation unit for the separation of olefin and inert gas,
f) a compressor for recycling the isolated olefin into the fluidized-bed polymerization reactor, and connecting lines between the devices a) to f).

BRIEF DESCRIPTION OF THE DRAWINGS

The invention is explained in greater detail below by way of example with reference to the single figure shown in the attached drawing.

FIG. 1 shows a flow chart of a polyolefin plant having an apparatus for the isolation of polyolefins.

DETAILED DESCRIPTION OF THE PREFERRED EMBODIMENTS

In the polyolefin plant shown in FIG. 1, the gas-phase polymerization takes place in polymerization reactor 1. The catalyst is introduced into the polymerization reactor 1 together with the inert gas, the catalyst being added in the form of particles at feed point 2 and the inert gas at feed point 3. An offgas line 4 and the discharge pipe 5 for gas fed back to the reactor as circulation gas are located in the upper region of the polymerization reactor 1. The inlet pipe for fluidization gas 6, to which inert gas is fed at feed point 7 and gaseous monomer at feed point 8, is located beneath the polymerization reactor 1. Fluidization gas introduced into the lower region of the polymerization reactor 1 is distributed at a gas distributor plate 9 in such a way that a stable fluidized bed forms in the polymerization reactor 1.

The polyolefin forming the polymerization reactor 1 is fed into the discharge tank 10 together with the gases present in the polymerization reactor 1. In the discharge tank 10, the gases are separated from the polymer. The polymer is transferred into a purification tank 11, with inert gas being blown into the purification tank 11 from the feed points 12 for purification. The gas arising in the purification tank 11, which predominantly comprises inert gas, is, before being liberated as offgas at the discharge point 13, passed through a filter 14 for the retention of fine polymer particles. The polymer formed in the polymerization reactor 1 is obtained at the outlet 15.

The gas mixture separated off from the polymer in the discharge tank 10 is freed from fine polymer particles in a further filter 16. The gas mixture is subsequently passed through an apparatus 17 for the removal of catalyst poisons, for example a device which contains one or more molecular sieves. The gas mixture from which catalyst poisons have been removed is separated into inert gas and olefin in a separation unit 18 (for example a membrane device). However, this separation is not complete, and consequently the separated-off olefin still contains inert gas (residues) and the separated-off inert gas still contains olefin (residues). The inert gas is discharged through the discharge pipe 19 and can subsequently be employed as stripping gas (preferably in the same process), it being possible for the inert gas as stripping gas to be introduced into the discharge tank 10 and/or into the purification tank 11 (for example via feed points 12) via lines which are not shown.

The isolated olefins are introduced with the aid of a gas compressor 20 into the circulation-gas stream, which also contains the reactor gas discharged through the discharge pipe 5. The circulation gas is passed by means of a second gas compressor 21 through a heat exchanger 22, in which the hot gas is cooled and subsequently provided as fluidization gas to the polymerization reactor 1.

In a further embodiment of the invention, the apparatus 17 for the removal of the catalyst poison may be installed downstream of the separation unit 18 (separation of olefins and inert gases). In such a case, which is not shown in the figure, exclusively the separated-off olefin is passed through the apparatus 17 for the removal of the catalyst poison.

The method according to the invention for the isolation of olefins from polyolefin plants can be used not only specifically in gas-phase polymerization, but in principle in all polymerization techniques which are suitable for the polymerization of polyolefins, such as, for example, solution or suspension polymerization. Under the conditions indicated in detail above, it operates reliably, effectively and under economical conditions.

What is claimed is:

1. A method for the isolation of olefins from a gas mixture comprising one or more olefins, an inert gas and a catalyst poison, where the gas mixture is fed to a separation unit and separated into olefin and inert gas, wherein an apparatus for removal of catalyst poison is installed upstream or downstream of the separation unit, such that
   (i) in the case where an upstream apparatus is installed upstream, the catalyst poison is at least partially removed from the gas mixture, and
   (ii) in the case where an apparatus is installed downstream, the catalyst poison is at least partially removed from separated olefin.

2. The method of claim 1, wherein the gas mixture is obtained as offgas in the catalytic gas-phase polymerization of olefins.

3. The method of claim 1 wherein the separation unit is a distillation device or a membrane device which contains at least one membrane.

4. The method of claim 3, wherein the separation unit is a membrane device, which is in the form of a spiral, wound or flat module, said separation unit having an operating temperature of from −30 to 100° C.

5. The method of claim 1 wherein said apparatus is a device comprising at least one molecular sieve.

6. The method of claim 1, wherein said olefin comprises either ethylene or propylene.

7. The method of claim 1, wherein said inert gas comprises nitrogen.

8. The method of claim 1, wherein a percentage of catalyst poison in the gas mixture is less than or equal to $10^{-3}$% by weight, and wherein the catalyst poison removed from the gas mixture is sulfur dioxide.

9. The method of claim 1, wherein the gas mixture consists essentially of inert gas and olefin, with the gas mixture comprising from 20 to 80% by volume of olefin.

10. The method of claim 9, wherein said gas mixture comprises from 40 to 60% by volume of olefin.

11. An apparatus comprising
    a polymerization reactor,
    a discharge tank operatively connected to said polymerization reactor,
    a filter for retention of fine polymer particles,
    an apparatus for removal of a catalyst poison;
    a separation unit for separation of olefin and inert gas;
    a gas compressor for recycling isolated olefin into said polymerization reactor.

* * * * *